(12) United States Patent
Park et al.

(10) Patent No.: US 7,566,553 B2
(45) Date of Patent: Jul. 28, 2009

(54) **MICROORGANISM OF *ESCHERICHIA* SP, OR *CORYNEBACTERIUM* SP, COMPRISING FOREIGN NADP DEPENDENT GLYCERALDEHYDE-3-PHOSPHATE DEHYDROGENASE GENE AND METHOD FOR PRODUCING L-LYSINE USING THE SAME**

(75) Inventors: Young-Hoon Park, Seongnam (KR); So-Yeon Rah, Seoul (KR); Seong-Jun Kim, Suwon (KR); Mun-Su Rhee, Icheon (KR)

(73) Assignee: CJ Corporation, Seoul (KR)

( * ) Notice: Subject to any disclaimer, the term of this patent is extended or adjusted under 35 U.S.C. 154(b) by 0 days.

(21) Appl. No.: 11/722,820

(22) PCT Filed: Dec. 29, 2005

(86) PCT No.: PCT/KR2005/004625

§ 371 (c)(1),
(2), (4) Date: Jun. 26, 2007

(87) PCT Pub. No.: WO2006/071086

PCT Pub. Date: Jul. 6, 2006

(65) Prior Publication Data

US 2008/0138882 A1    Jun. 12, 2008

(30) Foreign Application Priority Data

Dec. 30, 2004  (KR) .................. 10-2004-0116999

(51) Int. Cl.
C12P 13/08  (2006.01)
C12N 9/00   (2006.01)
C12N 9/02   (2006.01)
C12N 1/20   (2006.01)
C07H 21/04  (2006.01)

(52) U.S. Cl. ............... 435/115; 435/183; 435/189; 435/252.3; 435/320.1; 536/23.2

(58) Field of Classification Search ............... None
See application file for complete search history.

(56) References Cited

U.S. PATENT DOCUMENTS 6,632,644 B2  10/2003  Möckel et al.
6,713,289 B2  3/2004  Möckel et al.

FOREIGN PATENT DOCUMENTS

| EP | 0723011 A1 | 7/1996 |
| EP | 0733710 A1 | 9/1996 |
| EP | 1253195 A1 | 10/2002 |
| KR | 1992-0012444 B1 | 9/1992 |

OTHER PUBLICATIONS

Houchins et al. Immunogenetics. 1993;37(2):102-7.*
Valverde et al. FEBS Lett. Apr. 23, 1999;449(2-3):153-8.*
Krömer et al. J Bacteriol Mar. 2004;186(6): 1769-84.*
GenBank NP_350239, published Jul. 22, 2008.*
Abdelghani Iddar, et al.: "Expression, purification, and characterization of recombinant nonphosphorylating NADP-dependent glyceraldehyde-3-phosphate dehydrogenase from *Clostridium acetobutylicum*," Protein Expression and Purification, vol. 25, 2002, pp. 519-526.
Federico Valverde, et al.: "Engineering a central metabolic pathway: glycolysis with no net phosphorylation in an *Escherichia coli* gap mutant complemented with a plant GapN gene," FEBS Letters, vol. 449, 1999, pp. 153-158.
Darrel H. Spackman, et al.: "Automatic Recording Apparatus for Use in the Chromatography of Amino Acids," Analytical Chemistry, vol. 30, No. 7, Jul. 1958, pp. 1190-1201.
Abdelghani Iddar, et al.: "Purification of recombinant non-phosphorylating NADP-dependent glyceraldehyde-3-phosphate dehydrogenase from *Streptococcus pyogenes* expressed in *E. coli*," Moleculr and Cellular Biochemistry, vol. 247, 2003, pp. 195-203.
http://www.ncbi.nlm.nih.gov/sites/entrez—Search results for "NP_350239", Aug. 20, 2008.
http://www.ncbi.nlm.nih.gov/sites/entrez—EntrezGene Full Report for CAC3657 NADP-dependent glyceraldehyde-3-phosphate dehydrogenase [*Clostridium acetobutylicum* ATCC 824] Gene ID:1119839, Aug. 20, 2008.

* cited by examiner

*Primary Examiner*—Christian L Fronda
(74) *Attorney, Agent, or Firm*—Rothwell, Figg, Ernst & Manbeck, P.C.

(57) ABSTRACT

Provided are an *Escherichia* species microorganism and *Corynebacterium* species microorganism that are transformed with a foreign NADP dependent glyceraldehydes-3-phosphate dehydrogenase gene and have the ability to produce L-lysine and a method of producing L-lysine using the microorganisms.

2 Claims, 1 Drawing Sheet

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
ggaccatagg gatcctttga aaata                                    25

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
tttctttata agtgtgagat tggattga                                 28
```

MICROORGANISM OF *ESCHERICHIA* SP, OR *CORYNEBACTERIUM* SP, COMPRISING FOREIGN NADP DEPENDENT GLYCERALDEHYDE-3-PHOSPHATE DEHYDROGENASE GENE AND METHOD FOR PRODUCING L-LYSINE USING THE SAME

CROSS-REFERENCE TO RELATED PATENT APPLICATION(S)

This application is a 35 U.S.C. § 371 National Phase Entry Application from PCT/KR2005/004652, filed Dec. 29, 2005, and designating the United States. This application also claims the benefit of Korean Patent Application No. 10-2004-0116999 filed on Dec. 30, 2004, in the Korean Intellectual Property Office, the disclosure of which is incorporated herein in its entirety by reference.

BACKGROUND OF THE INVENTION

1. Field of the Invention

The present invention relates to an *Escherichia* species microorganism or *Corynebacterium* species microorganism including a foreign NADP dependent glyceraldehydes-3-phosphate dehydrogenase gene and a method of producing L-lysine using the same.

2. Description of the Related Art

L-lysine is a kind of amino acid widely used for feed and medical supplies and is produced on an industrial scale using microorganisms. L-lysine has been produced by fermentation with strains, for example, *Corynebacterium*, especially *Corynebacterium glutamicum*. However, to compensate for disadvantages of *Corynebacterium*, it has been tried to use other microorganisms, for example, *Escherichia coli*. (*E. coli*). *Escherichia coli* is a gram negative microorganism that is scientifically and industrially most widely used. Since much research has been performed on *E. coli* by many researchers, and a larger amount of information on *E. coli* than on *Corynebacterium* is accumulated. An advantage of *E. coli* lies in that it is easy to handle the strain in a fermentation process. Therefore, research on the production of a large amount of L-amino acid using a wild type *E. coli* has been performed.

There has been research on an effect of the amplification of a L-lysine biosynthesis-related gene using a recombinant DNA technology on the synthesis of L-lysine and research on the improvement of L-lysine producing *E. coli* strain (EP0733710A1 and EP0723011 A1). For example, EP1253195A1 (Ajinomoto Co., Inc.) discloses that the productivity of lysine increases when the activity of enzyme, such as aspartate semialdehyde dehyrogenase, phosphoenolpyruvate carboxylase, transhydrogenase, and aspartase, increases. In addition, EP0733710A1 discloses a bacterium having mutant genes of dapA and lysC genes and further enhanced with dapB gene and a ddh gene.

Glyceraldehyde-3-phosphate dehydrogenases (GAPDH) involved in the in vivo carbon metabolism include a NAD dependent GAPDH acting in glycolysis, an NADP dependent GAPDH, and a nonphosphorylation NADP-dependent □lyceraldehydes-3-phosphate dehydrogenase (GapN) (Iddar, A, et al., Protein Expr Purif. 25(3): 519-26 (2002)). L-lysine in *E. coli* is synthesized from L-aspartate through 9 enzymatic reaction steps, two of which are NADPH-dependent steps. The concentration of NADPH in cell affects the synthesis of L-lysine. In other words, a larger amount of L-lysine can be produced by increasing the concentration of NADPH in cell. Therefore, when an enzyme GapN, which does not inherently exist in *E. coli*, is introduced and expressed, there is a possibility of increase in the concentration of NADPH in cell. In addition, Valverde, F. et al. introduced a *Clostridium acetobutylicum*-derived gapN gene into *E. coli* to express the gene (FEBS Lett. 449, 153-158 (1999)).

However, conventionally, there has never been an example of developing a strain with improved L-lysine productivity by introducing the gapN gene into a L-lysine producing microorganism.

The inventors of the present invention has found that the productivity of a L-lysine producing strain can be improved by introducing a *Clostridium acetobutylicum*-derived gapN gene into the strain and completed the present invention.

SUMMARY OF THE INVENTION

The present invention provides a L-lysine producing microorganism including a foreign NADP dependent glyceraldehydes-3-phosphate dehydrogenase gene.

The present invention provides a method of producing L-lysine using the microorganism.

According to an aspect of the present invention, there are provided an *Escherichia* species microorganism and *Corynebacterium* species microorganism that are transformed with a foreign NADP dependent glyceraldehyde-3-phosphate dehydrogenase gene and can produce L-lysine.

In the present invention, the foreign NADP dependent glyceraldehyde-3-phosphate dehydrogenase (gapN) gene can be any gene coding a polypeptide having the activity of converting glyceraldehyde-3-phosphate serving as a substrate into 3-phosphoglycerate. Examples of the foreign gapN gene include genes derived from plants including corn (GeneBank Accession No.: X75326) and microorganisms including *Clostridium acetobutylicum* (GeneBank Accession No.: NP_350239).

In the present invention, examples of the *Escherichia* sp. microorganism include *Escherichia coli*. Examples of the *Corynebacterium* sp. microorganism include, but are not limited to, *Corynebacterium glutamicum*, *Corynebacterium thermoaminogenes*, *Brevibacterium flavum*, and *Brevibacterium lactofermentum*. The *Escherichia* sp. microorganism according to the present invention may be *Escherichia coli* CJ40226 (Accession No. KCCM-10628).

An *E. coli* strain capable of producing L-lysine according to the present invention may include a gene sequence (GeneBank Accession No. NP_350239) of the NADP dependent glyceraldehyde-3-phosphate dehydrogenase of *Clostridium acetobutylicum*. The gene can be introduced into *E. coli* using a common method widely known in the art. For example, a transformed *E. coli* strain can be obtained by introducing the gene into a vector to obtain a recombinant vector and introducing the vector into *E. coli*. The recombinant vector can be prepared using a common method, for example, ligating the gene sequence of the NADP dependent glyceraldehyde-3-phosphate dehydrogenase of *Clostridium acetobutylicum* to a suitable vector using a restriction enzyme (BamHI). A vector that can be used in the present invention to prepare the recombinant vector may be derived from a vector, for example, a phage vector or plasmid vector, which can autonomously proliferate in bacteria, for example, in an *Escherichia* genus bacteria. Examples of the phage vector include pWE15, M13, λ EMBL3, λ EMBL4, λ FIXII, λ DASHII, λ ZAPII, λ gt10, λ gt11, Charon4A, Charon21A, etc. Examples of the plasmid vector include a pBR plasmid, a pUC plasmid, a pBluescriptII plasmid, a pGEM plasmid, a pTZ plasmid, a pET plasmid, a pMal plasmid, a pQE plasmid, etc.

In the present invention, an *Escherichia* sp. microorganism or *Corynebacterium* sp. microorganism into which the foreign NADP dependent glyceraldehyde-3-phosphate dehydrogenase gene is introduced according to the present invention can be a wild type strain or a mutant with an improved ability to produce L-lysine. Examples of the *Escherichia* sp. microorganism or *Corynebacterium* sp. microorganism include strains that nutritionally require methionine or are resistant to threonine analogues (for example, AHV (α-amino-β-hydroxy valeric acid)), lysine analogues (for example, AEC (S-(2-aminoethyl)-L-cysteine)), isoleucine analogues (for example, α-aminobutyric acid), methionine analogues (for example, ethionine), etc. In the present invention, an *Escherichia* sp. microorganism or *Corynebacterium* sp. microorganism into which the foreign NADP dependent glyceraldehyde-3-phosphate dehydrogenase gene is introduced according to the present invention can be a mutant with an improved ability to produce L-lysine that is obtained by increasing the number of copies of the gene or manipulating a gene regulatory sequence of the gene.

The present invention provides a method of producing L-lysine comprising culturing an *Escherichia* sp. microorganism or *Corynebacterium* sp. microorganism into which the foreign NADP dependent glyceraldehyde-3-phosphate dehydrogenase gene is introduced under conditions suitable for producing L-lysine. The culture conditions suitable for producing L-lysine include the kind of culture medium, culture temperature, etc., as well known to one of ordinary skill in the art. In addition, the produced L-lysine can be recovered from the culture using common methods of separating and purifying L-lysine that are known to one of ordinary skill in the art, for example, ion exchange chromatography, recrystallization, etc., but not limited thereto.

The term "transformation" used throughout the specification means that DNA is introduced into a host wherein the DNA remains as an extrachromosomal element or integrated into the chromosome and is made to be replicable. The term "transfection" used throughout the specification means that an expression vector having an arbitrary coding sequence which may be expressed or not is received by a host cell. The terms "transfected host" and "transformed host" used throughout the specification means a cell into which DNA is introduced. The term "vector" refers to a DNA product having a DNA sequence operably linked to a regulatory sequence that can express DNA in a suitable host. Examples of the regulatory sequence include a promoter for transcription, an arbitrary operator sequence for regulating transcription, a sequence encoding an appropriate mRNA ribosome binding site, and sequences for regulating the termination of transcription and translation. Examples of the vector include plasmids, phage particles, or simply potential genomic inserts. Once transformed into a suitable host, the vector may replicate and function independently of the host genome, or may, in some instances, integrate into the genome itself. As used herein, "plasmid" and "vector" are sometimes used interchangeably as the plasmid is the most commonly used form of vector at present. The term "regulatory sequence" refers to a DNA sequence necessary for the expression of the operably linked coding sequence in a particular host organism. For example, regulatory sequences necessary for expression in prokaryotes include a promoter, optionally an operator sequence, and a ribosome binding site.

A method of producing a L-lysine-producing strain and a method of producing L-lysine using the strain will be described.

To develop a lysine-producing strain, an *Escherichia coli* TF1 (Korean laid-open Patent No. 1992-0012444) as a parent strain is treated using N-methyl-N'-nitro-nitrosoguanidine as a mutagen. The *E. coli* strain at an exponential growth phase was suspended in a 0.1M phosphate buffer (pH 7.0) or 0.1M citrate buffer solution (pH 5.5), and N-methyl-NN'-nitro-N-nitrosoguanidine is added into the suspension to a final concentration of 200-500 µg/mL and reacted at 30° C. for 10-30 minutes to induce mutation. Next, a minimum agar plate to which 1-30 g/L of a lysine analogue, AEC (S-(2-aminoethyl)-L-cysteine)), is added is inoculated with the solution and incubated at 30-37° C. for a few days to obtain analogue-resistant strains. The resulting analogue-resistant strains nutritionally require methionine or are resistant to threonine analogues (for example, AHV (α-amino-β-hydroxy valeric acid)), lysine analogues (for example, AEC (S-(2-aminoethyl)-L-cysteine)), isoleucine analogues (for example, α-aminobutyric acid), methionine analogues (for example, ethionine), etc. Selected strains are cultured under aerobic conditions (shaking culture at 250 rpm and 33° C.) for 60 hours to produce L-lysine.

The L-amino acid can be analyzed using anion exchange chromatography and subsequent ninhydrine derivatization (Spackman et al. Analytical Chemistry, 30 (1958), 1190).

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
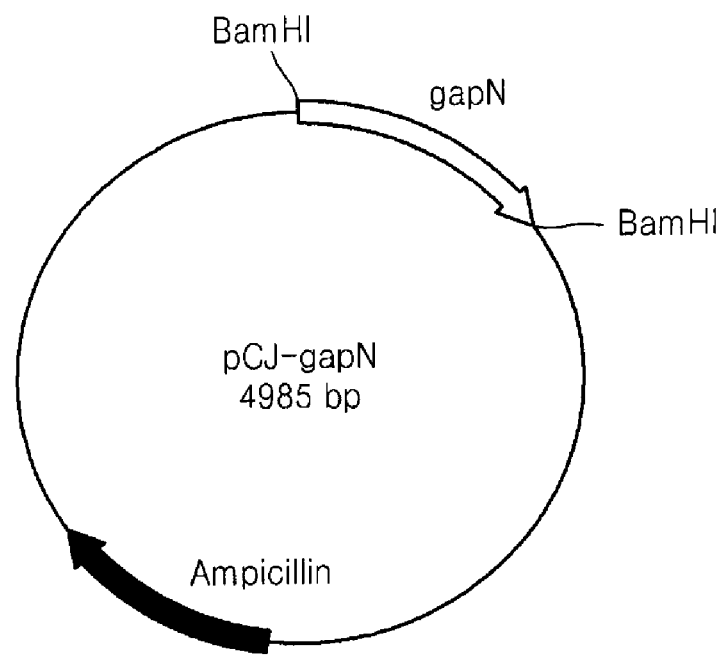
FIG. 1 is a map of an expression vector pCJ-gapN used to introduce a foreign NADP dependent glyceraldehyde-3 phosphate dehydrogenase gene derived from *Clostridium acetobutylicum* into *E. coli* in an example according to the present invention.

Hereinafter, the present invention will be described in more detail with reference to the following examples. However, the following examples are for illustrative purposes only and are not intended to limit the scope of the invention.

EXAMPLES

Example 1

Preparation of Lysine-Producing *E. coli* Strain K225 and Confirmation of its Characteristics An *Escherichia coli* strain TF1 (Korean laid-open Patent No. 1992-0012444) was grown until the strain entered an exponential growth phase and suspended in a 0.1M phosphate buffer (pH 7.0) or 0.1M citrate buffer solution (pH 5.5). N-methyl-N'-nitro-nitrosoguanidine was added into the suspension to a final concentration of 200-500 µg/mL, reacted at 30° C. for 10-30 minutes, and inoculated into a minimum agar plate containing 1-30 g/L of a lysine analogue (AEC: S-(2-aminoethyl)-L-cysteine) to select an analogue-resistant strain. This strain was named "CJ40225". The resistance of the strain against the lysine analogue was tested using an M9 minimum medium, and the relative growth rate was measured. The results are shown in Table 1.

TABLE 1

Relative Growth Rates of Wild type *E. coli* strain, TF1, and CJ40225 with respect to the concentration of AEC

| | Relative Growth Rate (%)* Concentration of added AEC (g/L) | | | | |
|---|---|---|---|---|---|
| Strain | 0 | 5 | 10 | 20 | 40 |
| W3110 | 100 | 66.3 | 39.8 | 7.4 | — |
| TE1 | 100 | 103.5 | 128.9 | 112.5 | 17.5 |
| CJ40225 | 100 | 124.3 | 88.4 | 89.2 | 73.9 |

*The relative growth rate was measured as absorbance of a culture solution at 562 nm and expressed as a percentage with respect to growth rate at a zero concentration of AEC.

The used M9 minimum medium contained 4 g of glucose, 12.8 g of $Na_2HPO_4.7H_2O$, 3 g of $KH_2PO_4$, 0.5 g of NaCl, and 1 g of $NH_4Cl$ per 1 liter of water.

To measure the L-lysine conductivity of the screened *E. coli* strain CJ40225, the strain CJ40225 was cultured as follows.

Each of the *E. coli* producing strain TF1 and the *E. coli* strain CJ40225 was inoculated into 25 mL of seed medium with the composition below contained in a 250 mL corner-baffled flask and incubated at 33° C. for 60 hours while shaking at 250 rpm. After the incubation was completed, the amount of produced L-lysine was measured using HPLC. The amount of L-lysine in each of the cultures obtained with W3110, TF1, and CJ40225 is shown in Table 2.

The used production medium (pH 7.0) contained 60 g of glucose, 2 g of yeast extract, 17 g of $(NH_4)_2SO_4$, 0.3 g of $KH_2PO_4$, 0.6 g of $K_2HPO_4$, 1 g of NaCl, 1 g of $MgSO_4.H_2O$, 10 mg of $FeSO_4.H_2O$, 10 mg of $MnSO_4.H_2O$, 30 g of $CaCO_3$, 0.05 g of L-isoleucine, and 0.6 g of L-methionine per 1 liter of water.

TABLE 2

Results of Fermentation in Flask using the wild type *E. coli* strain W3110, TF1, and W3

| Strain | Lysine monohydrochloride concentration (g/L) | Threonine concentration (g/L) |
|---|---|---|
| W3110 | — | — |
| TF1 | 5.4 | 3.0 |
| CJ40225 | 1.2 | 8.3 |

Example 2

Screening and Cloning of NADP Dependent glyceraldehyde-3-phosphate dehydrogenase Gene (gapN) Derived from *Clostridium*

The sequence of a NADP dependent glyceraldehyde-3-phosphate dehydrogenase (gapN) gene derived from *Clostridium* had been identified. Information on an NADP dependent glyceraldehyde-3-phosphate dehydrogenase gene (gapN) of *Clostridium acetobutylicum* with Accession No. NP_350239 was obtained from the NIH GenBank. PCR was performed using oligonucleotides of SEQ ID Nos. 1 and 2 as primers and a chromosomal DNA of a *Clostridium acetobutylicum* ATCC 824 strain as a template based on the gene sequence information to amplify the NADP dependent glyceraldehyde-3-phosphate dehydrogenase gene (gapN) to 1485 bp. During the PCR, a cycle of denaturation 94° C. for 30 seconds, annealing at 51° C. for 30 seconds, and polymerization at 72° for 1 minute was repeated 25 times. The resulting PCR products were cloned with *E.coli* plasmid pCR2.1 using a TOPO Cloning Kit (Invitrogen Corp.) to obtain a pCR-gapN plasmid.

Example 3

Figure 2:
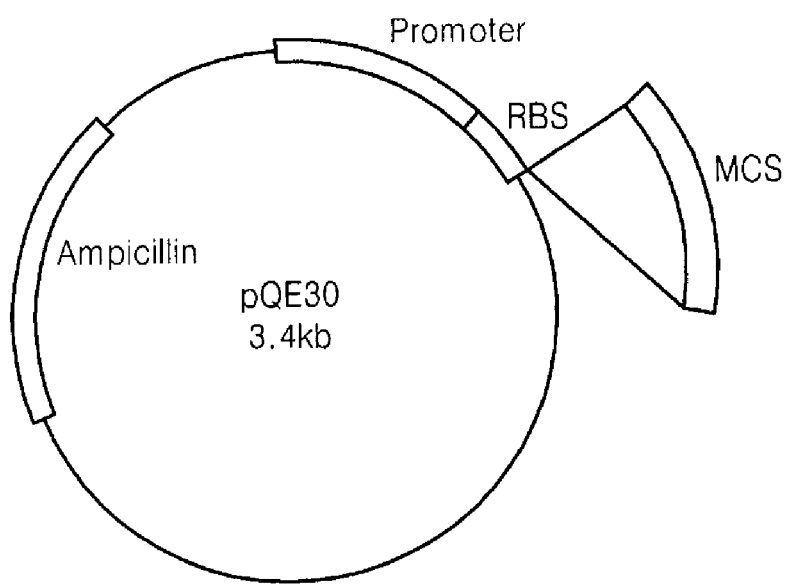
FIG. 2 is a map of an *E. coli* expression vector pQE30.

Construction of NADP Dependent glyceraldehyde-3-phosphate dehydrogenase Gene Expression Vector The vector pCR-gapN containing the NADP dependent glyceraldehyde-3-phosphate dehydrogenase gene obtained in Example 2 was cleaved with a restriction enzyme BamHI to separate only a gene fragment encoding NADP dependent glyceraldehyde-3-phosphate dehydrogenase. The gene fragment was ligated to an *E. coli* expression vector pQE30 (Qiagen Corp.) using a ligation enzyme to enable the gene to be expressed in cells by a T5 promoter of bacteriophage existing in the vector. FIG. 2 is a map of the vector PQE30. Next, an *E. coli* DH5α strain was transformed through heat shocking and cultured in a Lurina-Bertani (LB) agar medium containing 100 µg/mL of ampicillin to screen transformed strains. The expression vector pCJ-gapN was separated from each of the transformed strains.

Example 4

Confirmation of Expression of NADP Dependent glyceraldehyde-3-phosphate dehydrogenase Protein in *E. coli* Transformed with pCJ-gapN The transformed *E. coli* DH5α (pCJ-CFK) containing pCJ-gapN was cultured in a LB medium containing antibiotic ampicillin for one day. A portion of the culture solution was inoculated into a LB medium containing ampicillin and cultured until the transformed entered an initial stationary phase. The culture solution in the initial stationary phase was centrifuged to separate cells, suspended in a suitable buffer, and disrupted using ultrasonic waves, and centrifuged at a high speed to obtain a supernatant. A portion of the supernatant was used to measure the expression of the protein through SDS-PAGE. As a result, an overexpression of protein in a band of 52.5 Kd corresponding to the molecular weight of the NADP dependent glyceraldehyde-3-phosphate dehydrogenase was observed.

Example 5

Activity Measurement of NADP Dependent glyceraldehyde-3-phosphate dehydrogenase

A complementation test was performed to determine whether the NADP dependent glyceraldehyde-3-phosphate dehydrogenase protein identified in Example 4 had an enzymatic activity in cells.

A mutant strain in which the glyceraldehyde-3-phosphate dehydrogenase of *E. coli* has no activity can grow in a medium to which glycerol and succinic acid are added as carbon sources but cannot grow in a LB medium. When this mutant strain is transformed with the vector pCJ-gapN that can express the NADP dependent glyceraldehyde-3-phosphate dehydrogenase so that the NADP dependent glyceraldehyde-3-phosphate dehydrogenase has a normal enzymatic activity, the mutant strain can grow in a LB medium.

A mutant strain DS122 (CGSC strain #7566) in which the glyceraldehyde-3-phosphate dehydrogenase of *E. coli* has no activity was obtained from Yale University *E. coli* Genetic Stock Center, transformed through heat shocking and cultured in a minimum medium containing glycerol, succinic acid, and chloramphenicol to screen a transformed strain. The resultant transformed strain was inoculated in a LB medium, and it was checked whether it could grow in the medium. As a result, it was confirmed that the transformed strain can grow in the LB medium unlike other mutants. Next, the expression of the glyceraldehyde-3-phosphate dehydrogenase protein in the transformed strain grown in the LB medium was confirmed through SDS-PAGE.

Example 6

Preparation of L-lysine Producing Strain Including pCJ-gapN and Production of L-lysine The L-lysine producing *E. coli* strain CJ40225 prepared in Example 1 was transformed with the NADP dependent glyceraldehyde-3-phosphate dehydrogenase expression vector pCJ-gapN confirmed in Example 5 through heat shocking to obtain a transformed strain. The transformed strain was named "CJ40226". It was checked whether the transformed strain CJ40336 included a plasmid. Next, the transformed strain CJ40336 was cultured in the same manner as in Example 1, and the concentration of L-lysine produced in the medium was measured. The amount of the produced L-lysine is shown in Table 3. *E. coli* strain CJ40225 was used as a control.

TABLE 3

Amounts of L-lysine produced from *E. coli* strains CJ40225 and CJ40226

| Strain | Lysine monohydrochloride concentration (g/L) |
|---|---|
| CJ40225 | 8.3 |
| CJ40226 | 10.8 |

Referring to Table 3, the *E. coli* strain CJ40226 including a foreign NADP dependent glyceraldehyde-3-phosphate dehydrogenase gene derived from *Clostridium acetobutylicum* has a higher lysine productivity than the strain CJ40225 not including the gene. The inventors of the present invention deposited the *E. coli* CJ40226 into the Korean culture Center of Microorganisms (KCCM) under the Budapest Treaty on Nov. 30, 2004 with Accession No. KCCM-10628.

As described above, the *Escherichia* sp. microorganism and the *Corynebacterium* sp. microorganism according to the present invention have highly improved L-lysine productivity. In addition, L-lysine can be efficiently produced using the method according to the present invention While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An isolated *Escherichia coli* CJ40226 of Accession number KCCM-10628.

2. A method of producing L-lysine comprising culturing the *E. coli* according to claim 1 and recovering L-lysine produced from the culture.

* * * * *